US005849014A

United States Patent [19]
Mastrorio et al.

[11] Patent Number: 5,849,014
[45] Date of Patent: Dec. 15, 1998

[54] CEMENT RESTRICTOR SYSTEM AND METHOD OF FORMING A CEMENT PLUG WITHIN THE MEDULLARY CANAL OF A BONE

[75] Inventors: Brooke W. Mastrorio, Lakeville; Pierre S. Ostiguy, Rochester, both of Mass.

[73] Assignee: Johnson & Johnson Professional, Inc., Raynham, Mass.

[21] Appl. No.: 821,608

[22] Filed: Mar. 20, 1997

[51] Int. Cl.[6] ................................................ A61B 17/56
[52] U.S. Cl. ................................................ 606/94; 606/95
[58] Field of Search ................................. 606/95, 94, 93, 606/92, 86

[56] References Cited

U.S. PATENT DOCUMENTS

| | | |
|---|---|---|
| 4,245,359 | 1/1981 | Stuhmer . |
| 4,276,659 | 7/1981 | Hardinge . |
| 4,302,855 | 12/1981 | Swanson . |
| 4,344,190 | 8/1982 | Lee et al. . |
| 4,399,814 | 8/1983 | Pratt, Jr. et al. ........................... 606/94 |
| 4,447,915 | 5/1984 | Weber . |
| 4,462,394 | 7/1984 | Jacobs . |
| 4,559,936 | 12/1985 | Hill . |
| 4,686,973 | 8/1987 | Frisch . |
| 4,697,584 | 10/1987 | Haynes . |
| 4,745,914 | 5/1988 | Frey et al. . |
| 4,815,454 | 3/1989 | Dozier, Jr. ................................... 606/94 |
| 5,092,891 | 3/1992 | Kummer et al. ........................... 623/16 |
| 5,340,362 | 8/1994 | Carbone ..................................... 623/23 |
| 5,468,245 | 11/1995 | Vargas, III et al. ....................... 606/94 |

*Primary Examiner*—Guy V. Tucker
*Attorney, Agent, or Firm*—Nutter, McClennen & Fish, LLP

[57] ABSTRACT

A cement restrictor system is provided for making a cement plug within the medullary canal of a long bone. The system includes an inflatable body, a conduit having first and second ends that defines a fluid passage to and from the inflatable body, and a shield releasably securable to the conduit. In an exemplary method of making a cement plug with the system an obstruction, such as the shield, is placed in a medullary canal of a long bone beyond the isthmus of the long bone. The obstruction is held in place with the flatable body. A predetermined quantity of bone cement is poured into the medullary canal and localized by the obstruction. The bone cement is allowed to harden; and the conduit and inflatable body are removed from the bone.

22 Claims, 2 Drawing Sheets

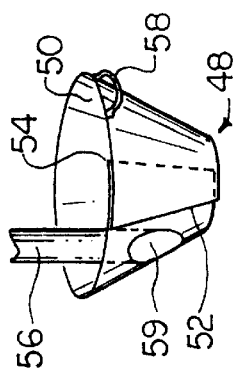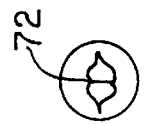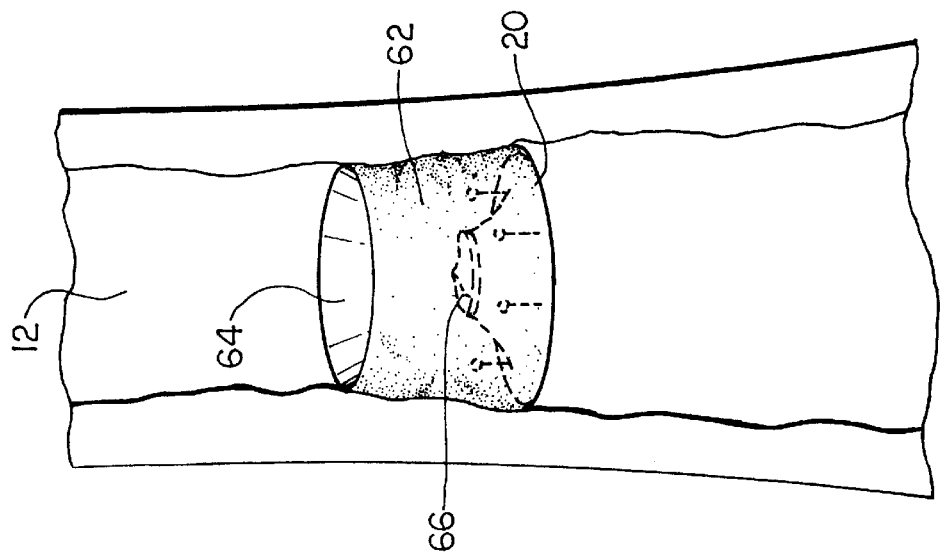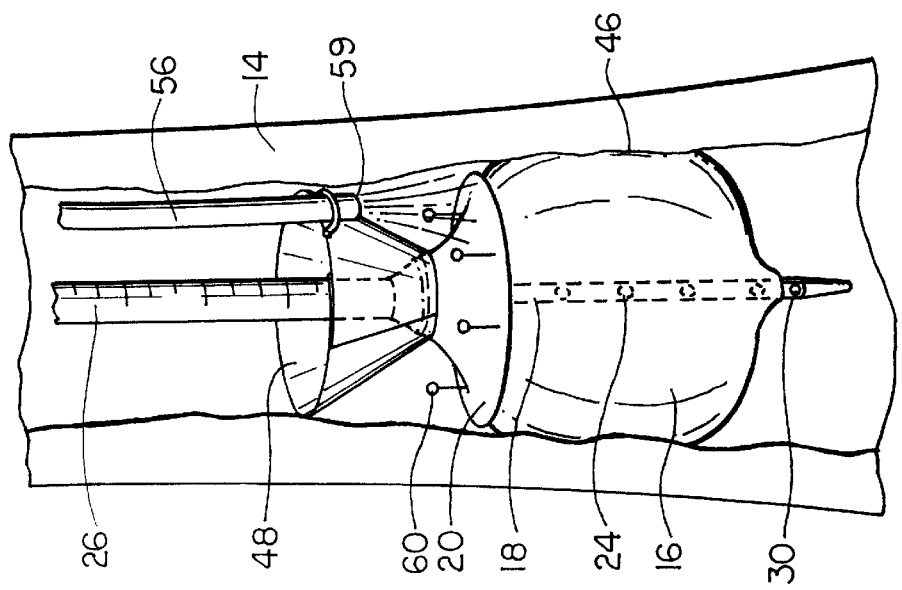

CEMENT RESTRICTOR SYSTEM AND METHOD OF FORMING A CEMENT PLUG WITHIN THE MEDULLARY CANAL OF A BONE

CROSS REFERENCE TO RELATED APPLICATIONS

Not Applicable.

STATEMENT REGARDING FEDERALLY-SPONSORED RESEARCH

Not Applicable.

FIELD OF THE INVENTION

The present invention relates to a device used in hip arthroplasty, and more particularly to a system for creating a cement plug within a medullary canal of a long bone.

BACKGROUND OF THE INVENTION

Arthroplasty procedures, such as a total hip replacement, can require the removal of the femoral head and neck, followed by implantation of an artificial hip stem into a reamed portion of the femoral medullary canal. Some hip arthroplasty procedures call for the use of bone cement to secure the hip stem within the medullary canal. For procedures that call for cement, it is generally undesirable to allow the cement to infiltrate the medullary canal to an uncontrolled depth and volume. Therefore, a hip arthroplasty procedure can include the step of placing an obstruction within the medullary canal in an attempt to restrict or block the flow of cement.

Not infrequently, the obstruction is merely a partially hardened or cured ball of cement shoved into the canal and held in place by friction fit with the wall of the canal. This makeshift obstruction is easily dislodged by the distal end of the hip stem if the cement ball is not inserted deep enough into the canal. Additionally, the ball of cement is readily displaced when pressurized cement is added to the medullary canal to bind the stem in place. If the cement ball is fractured and/or if it falls beyond a narrow central region of the femur known as the isthmus, the pressurized cement does not properly infiltrate the bone and air pockets or pores are created in the cement. The imperfection laden hardened cement thus provides a poor interlock with the bone and stem and it is susceptible to cracking. Poor mechanical interlock and cement failure causes the stem to loosen. This undesirable occurrence often requires that the joint be replaced in a procedure known as a revision.

Revision surgery and/or procedures requiring a "long" hip stem are especially problematic with respect to procedures requiring pressurized cement application. Specifically, the distal end of a revision stem ultimately extends further into the medullary canal than an original "normal" stem because additional bone is cut-away during removal of the original stem in preparation to prepare for implantation of the revision stem, or poor quality bone stock forces a larger stem to be utilized to secure the stem more distally in the canal to reach better quality bone to achieve implant stability. Whereas the distal end of the original stem may extend to a point before or above the isthmus, and thus above the ball of cement, the distal end of the revision stem may extend beyond the isthmus. Although it would be desirable to have a cement plug that infiltrates the bone and which is firmly held in place beyond the isthmus, it is not possible to accomplish this by merely shoving a ball of partially hardened cement into the medullary canal.

SUMMARY OF THE INVENTION

The present invention overcomes the disadvantages of known techniques and devices by providing a cement restrictor system that is particularly well suited for revision arthroplasty. The system allows for the creation of a cement plug at any selected point within a long bone, including points beyond the isthmus.

The cement restrictor system includes an inflatable body, a conduit defining a fluid passage to and from the inflatable body, and a shield or obstruction releasably securable to the conduit. The shield can include a plurality of protuberances that promote bonding of the shield to bone cement deposited thereon. A collar is positionable proximate the shield to define a space or boundary for a cement plug.

An illustrative embodiment of the system includes a rigid tubular guide having a first end and a second end. A flexible catheter having a first end and a second end is positionable at least partially within the tubular guide, and the second end of the flexible catheter is extensible from the second end of the tubular guide. An inflatable body surrounds a portion of the catheter proximate the second end of the catheter. A flexible shield is releasably securable to the rigid tubular guide at a point between the first end of the rigid tubular guide and the inflatable body. A collar that is positionable between the first end of the rigid tubular guide and the shield defines a space between the collar and the shield into which bone cement can be introduced.

In an exemplary procedure of the invention, a cement plug is formed beyond the isthmus of a bone by positioning a first obstruction in a medullary canal of a long bone beyond the isthmus of the long bone; holding the first obstruction in place with an inflatable body; depositing a predetermined quantity of bone cement into the medullary canal on the obstruction; and allowing the bone cement to harden.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 3 illustrates a collar used to define a cement boundary;

FIG. 4 illustrates the collar of FIG. 3 relative to other components of the cement restrictor system, wherein the inflatable body is in a fully inflated state;

FIG. 5 shows an exemplary cement plug formed in accordance with the invention; and FIGS. 6 and 7 depict sealing structures of a system component.

DETAILED DESCRIPTION OF THE INVENTION

Figure 1:
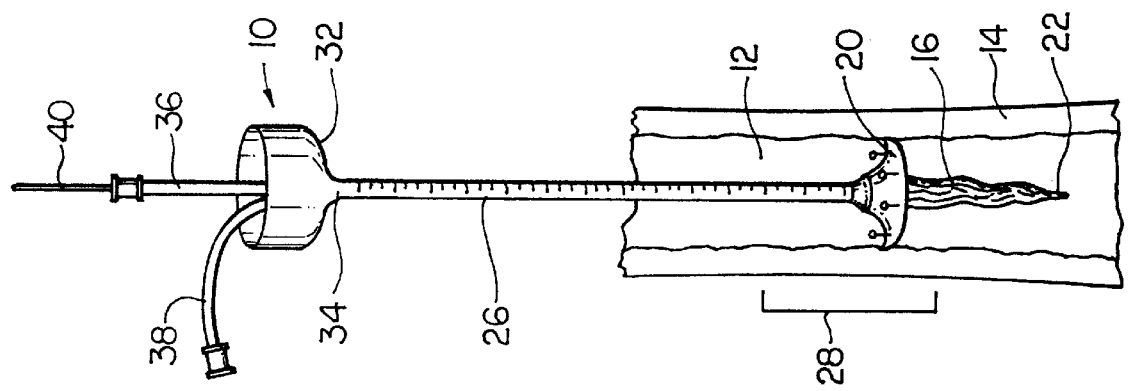
FIG. 1 is an illustration of a cement restrictor system in accordance with the present invention, wherein system components are shown partially inserted into a reamed bone portion.

FIG. 1 illustrates a cement restrictor system 10 (hereinafter "the system") in accordance with the invention being inserted within a reamed portion of a medullary canal 12 of a resectioned long bone 14, such as a femur. The system 10 includes an inflatable body 16, a conduit 18 (shown in FIGS. 2 and 4) in fluid communication with the inflatable body, and an obstruction or shield 20. In the illustration, the conduit 18 includes a flexible, single or multiple lumen catheter that is enveloped near a distal end 22 by the inflatable body 16. One or more openings 24 (shown in FIGS. 2 and 4) in the catheter 18 near the distal end 22 permit a fluid, such as a liquid or gas, to be introduced and evacuated from the inflatable body 16. In an exemplary embodiment, the conduit 18 and inflatable body 16 are provided by a catheter of the type useful in angioplasty procedures. An intermediate portion of such a catheter 18 with an integral inflatable body 16 is within an internal passage of a rigid or semi-rigid tubular guide 26. An apertured shield 20 abuts a distal end of the tubular guide 26 and a portion of the catheter 18 extends through the aperture and beyond the shield. All, or a portion of, the inflatable body 16 also extends beyond the aperture and the shield 20. In various embodiments the catheter 18 is the fluid conduit. However, in other embodiments the tubular guide 26 is the fluid conduit to and from the inflatable body 16.

The shield 20 is releasably engagable with the tubular guide 26 so that the tubular guide can be used to position the shield within the medullar canal 12 and then be separated from the shield. In one embodiment, the shield includes a shoulder portion against which a distal portion of the tubular guide seats to allow the tubular guide 26 to push the shield 20 into the medullary canal 12 beyond a constriction in the canal known as the isthmus 28. The shield 20 extends radially outward from the tubular guide 26 either perpendicularly or at an angle with respect to the tubular guide's longitudinal axis. At least the periphery of the shield 20 is resilient to allow the shield to be deformed and reduced in diameter a sufficient amount to pass through the isthmus 28 to an expanded region of the medullary canal 12 without damaging the bone 14. However, the shield can be smaller in outer diameter than the inner diameter of the isthmus, as the inflatable body can compensate for non-contact areas after inflation thereof. As illustrated, the outer edges of the shield 20 are upwardly bowed as pressure is applied to the shield by the tubular guide 26. The tubular guide 26 can include markings, such as measurement indicia, on the external surface thereof to help a surgeon determine the insertion depth of the tubular guide and the shield 20 within the bone. Additionally, the catheter 18 can include a radiopaque element 30 (shown in FIG. 4) to assist the surgeon in determining the extension distance of the distal end of the catheter from the tubular guide 26 and the shield 20. Additional radiopaque elements can be provided as desired to improve visualization of the catheter.

Figure 2:
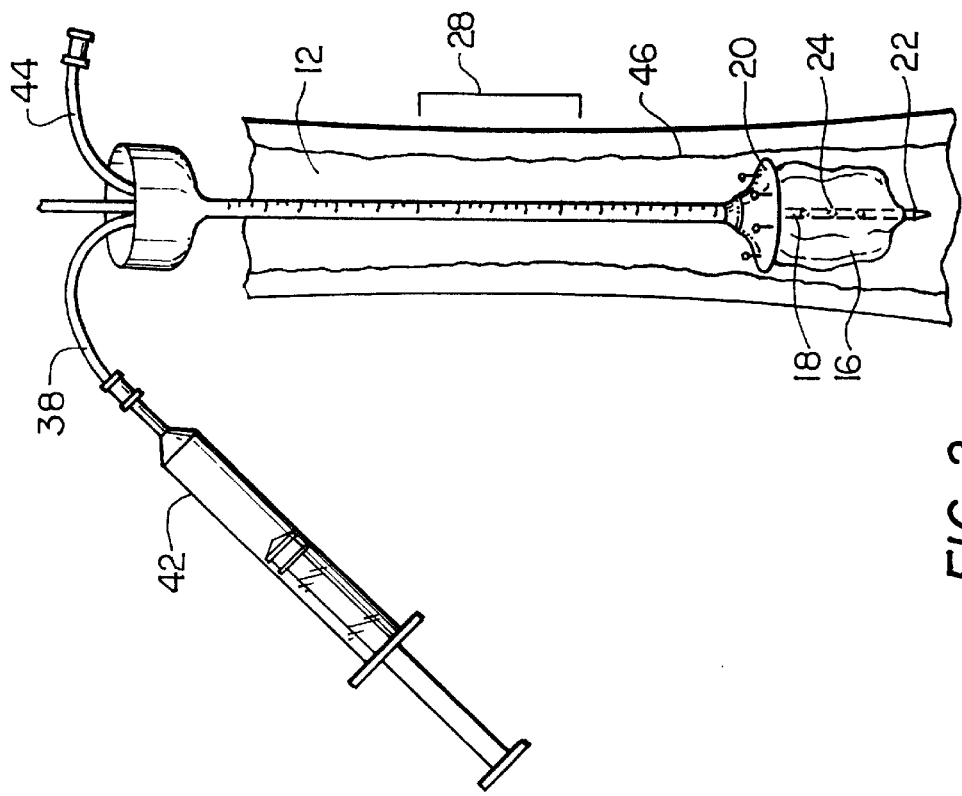
FIG. 2 is an illustration of the system shown in FIG. 1, wherein the system components are positioned for creation of a cement plug and an inflatable body is shown in a semi-inflated state.

To allow for the attachment of additional elements to the system 10 or to facilitate introduction of additional elements into the tubular guide 26 and/or the catheter 18, the embodiment of the system depicted in FIG. 1 further includes an optional manifold 32 securable to a proximal end 34 of the catheter or tubular guide 26. The manifold 32 provides a connection between a first port 36, a second port 38 and the tubular guide/catheter combination. Each of the ports can be associated with a respective lumen in a catheter having multiple lumens. For example, as shown in FIG. 1, the first port 36 permits introduction of a stiff rod 40 into the catheter 18 in order to impart rigidity to the catheter as desired. As shown in FIG. 2, the second port 38 is adapted for mating with a fluid introduction device such as a syringe 42. FIG. 2 also shows a third port 44 that is configured to permit access to the distal tip 22 of the catheter. Continuing to refer to FIG. 2, the shield 20 is shown positioned beyond the isthmus 28 and the periphery of the shield is in contact with a portion of the wall 46 of the medullary canal 12 where it will define a first cement boundary as described below. The inflatable body 16 is shown in a partially inflated state.

Referring now to FIG. 4, the inflatable body 16 is shown in a fully inflated state, wherein it presses outward against the wall 46 of the bone, thus limiting further downward travel of the shield 20 within the bone 14. It should be noted that the shield 20 is beyond the isthmus. Were it not for the inflatable body 16, there would be nothing to support the shield to retain it at a selected insertion depth in the absence of the tubular guide 26. The inflated collar also provides an additional seal against cement migration beyond the shield.

A collar 48 is positionable with respect to the shield 20, as shown in FIG. 4, to define a second cement boundary for cement that is injected, deposited, or allowed to flow into the space between the shield and the collar. The collar 48 can include an uninterrupted element, or, as shown in FIGS. 3 and 4, the collar can include a strip 50 having first and second overlapping free ends 52 and 54. The overlapping ends allow the collar 48 to be "opened" and wrapped around the tubular guide 26 at a point below the manifold 32. As shown, the collar 48 defines a frustroconical body having a central aperture. The smaller end of the collar 48 abuts the shield 20 and the wider end of the collar abuts the wall 46 of the bone 14.

As illustrated in FIG. 4, a cement supply tube 56 is positionable within the medullary canal so that a tube outlet 58 is capable of directing cement into the space between the collar 48 and the shield 20. A tube engagement device can be provided on the collar or the tube can join the cement supply tube 56 to the collar 48. As shown in FIG. 3, the engagement device can include an elastic loop 58 that binds the cement supply tube 46 to the collar 48. In another embodiment, an outlet 58 of the cement supply tube 56 is coincident with a hole in the strip 50. Thus, a rigid or semi-rigid cement supply tube 56 can be employed to push the collar through the medullary canal into an abutting relationship with the shield 20 after the shield has been fixed at a selected location by inflating the inflatable body 16.

Once the shield 20 and the collar 48 are positioned, cement is ejected from the outlet 58 until the space between the shield and the collar is substantially filled. Because the shield 20 is held so firmly in place by the inflatable body 16, the cement can be injected into the space under pressure to cause cement to infiltrate the bone 14. The collar 48 does not seal tightly against the bone in order to allow air displaced by the cement to escape from the space between the shield and the collar. In order to promote adhesion of the cement to the shield 20, one or more protuberances 60 can extend from the top surface of the shield. In exemplary embodiments, the protuberances 60 include a stalk 1 mm to 10 mm in length that terminates in an enlarged body. As the cement cures or hardens, the protuberances become trapped within the cement to bind the shield 20 to the cement, the cement infiltrates the surrounding bone, and a cement plug 62 is formed as shown in FIG. 5. The surface of the shield exposed to cement can be roughened or textured instead of, or in addition to, including protuberances 60. Because the shield 20 covers substantially all of the inflatable body 16, the cement does not bond to the inflatable body 16 at all or to an extent that would prevent it from being fully deflated and removed from the tubular guide 26. The balloon could be coated to prevent cement adhesion. The tip of the cement supply tube 56 and the cement facing side of the collar can be coated to prevent cement from bonding thereto.

After cement has been injected into the space between the shield 20 and the collar 48 and is sufficiently hard, the cement supply tube 56 and the collar 48 are removed from the medullary canal and the inflatable body 16 is deflated and withdrawn from the tubular guide 26. However, if desired, the cement supply tube 56 can be detached from the collar 48 and the collar, which can include surface features that bond with the cement, can remain in place as part of the cement plug 62. Finally, the tubular guide 26 is separated from the shield 20 and withdrawn from the medullar canal. The shield 20 remains affixed to the cement plug 62. Subsequently, as is known in the art, a femoral stem is placed into the medullary canal 12 and secured in place with bone cement. A sealing structure 66 prevents cement from passing through the central portion of the shield vacated by the tubular guide. FIG. 6 illustrates an exemplary sealing structure 66 that includes a first flap 68 that overlaps a second flap 70. FIG. 7 illustrates a sealing structure 66 that includes a "duck bill" with a central slit 72. Other structures are contemplated.

It will be noted in FIG. 5 that the frustroconical configuration of the collar 48 has defined a conical central recess 64 in the hardened cement plug. The recess 64 provides additional space for the distal end of the femoral stem to extend into the bone. The distal end of the stem can even penetrate the sealing structure 66 and be "centered" by the cement plug 62 and/or shield 20.

Although the invention has been shown and described with respect to exemplary embodiments thereof, various other changes, omissions and additions in form and detail thereof may be made without departing from the spirit and scope of the invention.

What is claimed is:

1. A cement restrictor system for providing a cement bone plug in the medullary canal of a bone, comprising:
   an inflatable body;
   a conduit having a first end and a second end, the conduit defining a fluid passage to the to the inflatable body for inflating and deflating the inflatable body; and
   a shield releasably securable to the conduit, the shield having a proximal surface for impeding the flow of bone cement and a distal surface for abutting the inflatable body, the shield and inflatable body being insertable in the medullary canal to form a seal therein allowing the formation of the cement bone plug adjacent the shield.

2. The cement restrictor system of claim 1, wherein the shield extends radially outward from the conduit.

3. The cement restrictor system of claim 2, wherein the proximal surface of the shield includes a plurality of protuberances extending therefrom for promoting adhesion of the bone cement to the shield.

4. The cement restrictor system of claim 3, wherein each of the protuberances includes a stalk having a first end secured to the shield and a second end having a greater diameter than the first end of the stalk.

5. The cement restrictor system of claim 2, wherein the promixal surface faces the first end of the conduit and is roughened.

6. The cement restrictor system of claim 1, wherein the shield is located at a point between the first end of the conduit and the inflatable body.

7. The cement restrictor system of claim 1, wherein the conduit includes:
   a rigid tubular guide having a first end and a second end, the second end being releasably securable to the shield, and
   a flexible catheter having a first end and a second end, the flexible catheter being disposed at least partially within the tubular guide,
   wherein the inflatable body surrounds a portion of the catheter between the shield and the second end of the conduit.

8. The cement restrictor system of claim 7, further including a radiopaque element proximate the second end of the flexible catheter.

9. The cement restrictor system of claim 7, further including a plurality of measurement indicia on an exterior portion of the rigid tubular guide.

10. The cement restrictor system of claim 1, wherein the shield defines an obstruction surface having a diameter greater than the diameter of an isthmus of a selected bone, and wherein the inflatable body is inflatable to a diameter greater than the diameter of the shield.

11. The cement restrictor system of claim 1, further comprising a collar that is positionable proximate the shield to define a space between the shield and the collar.

12. The cement restrictor system of claim 11, further comprising a cement supply tube for directing cement into the space between the shield and the collar.

13. The cement restrictor system of claim 12, wherein the cement supply tube is secured to the collar.

14. A cement restrictor system comprising:
   an inflatable body;
   a conduit having a first end and a second end, the conduit defining a fluid passage to the inflatable body; and
   a shield releasably securable to the conduit, the shield extending radially outward from the conduit, wherein the shield includes a frustroconical body that is flexible at its periphery.

15. The cement restrictor system of claim 14, wherein the frustroconical body includes sealing structure that defines an aperture through the shield.

16. The cement restrictor system of claim 15, wherein the sealing structure includes two opposed flexible elements.

17. A cement restrictor system comprising:
   an inflatable body;
   a conduit having a first end and a second end, the conduit defining a fluid passage to the inflatable body; and
   a shield releasably securable to the conduit,
   wherein the conduit includes:
      a rigid tubular guide having a first end and a second end, the second end being releasably securable to the shield, and
      a flexible catheter having a first end and a second end, the flexible catheter being disposed at least partially within the tubular guide,
   wherein the inflatable body surrounds a portion of the catheter between the shield and the second end of the conduit and the flexible catheter and the inflatable body can be passed through the rigid tubular guide from the second end of the rigid tubular guide to the first end of the rigid tubular guide.

18. A cement restrictor system comprising:
   a rigid tubular guide having a first end and a second end;
   a flexible catheter having a first end and a second end, the flexible catheter being positionable at least partially within the tubular guide, wherein the second end of the flexible catheter is extensible from the second end of the tubular guide;
   an inflatable body surrounding a portion of the catheter proximate the second end of the catheter, wherein the catheter defines a fluid path to and from the interior of the inflatable body;

a flexible shield releasably securable to the rigid tubular guide at a point between the first end of the rigid tubular guide and the inflatable body; and a collar that is positionable between the first end of the rigid tubular guide and the shield to define a space between the collar and the shield.

19. The cement restrictor system of claim 18, further including a cement supply tube for directing cement into the space between the shield and the collar, wherein the cement supply tube is securable to the collar.

20. A method of forming a cement plug comprising the steps of:

placing a first obstruction in a medullary canal of a long bone beyond the isthmus of the long bone;

holding the first obstruction in place with an inflatable body such that first obstruction and the inflatable body form a seal in the medullary canal that is effective to prevent the flow of bone cement;

depositing a predetermined quantity of bone cement into the medullary canal; and allowing the bone cement to harden to form a cement bone plug.

21. The method of claim 20, further comprising the step of deflating the inflatable body and removing the inflatable body from the long bone after the step of allowing the bone cement to harden.

22. The method of claim 20, further comprising the step of placing a second obstruction in the medullary canal in a spaced apart relationship with the first obstruction to define a space, and wherein the step of depositing includes the step of depositing the predetermined quantity of bone cement into the space defined by the first obstruction and the second obstruction.

* * * * *